United States Patent [19]

Mathiaparanam

[11] Patent Number: 5,039,821

[45] Date of Patent: Aug. 13, 1991

[54] PROCESS FOR PRODUCING DI[BIS-(INDOLYL)ETHYLENYL]TETRAHALOPHTHALIDES

[75] Inventor: Ponnampalam Mathiaparanam, Appleton, Wis.

[73] Assignee: Appleton Papers Inc., Appleton, Wis.

[21] Appl. No.: 561,839

[22] Filed: Aug. 2, 1990

Related U.S. Application Data

[63] Continuation-in-part of Ser. No. 397,703, Aug. 23, 1989, Pat. No. 4,970,308.

[51] Int. Cl.$^5$ .................. C07D 405/00; C07D 209/56

[52] U.S. Cl. .................................. 548/456; 544/58.1; 544/58.6; 544/142; 544/143; 546/200; 546/201; 548/427; 548/450; 548/451

[58] Field of Search ..................... 544/58.1, 143, 58.6, 544/142; 546/187, 200, 201; 548/427, 450, 451, 456

[56] References Cited

U.S. PATENT DOCUMENTS

| | | | |
|---|---|---|---|
| 4,016,174 | 8/1978 | Farber | 548/456 |
| 4,020,056 | 4/1977 | Farber | 548/456 |
| 4,020,068 | 4/1977 | Farber | 547/345 |
| 4,022,771 | 5/1977 | Farber | 548/456 |
| 4,107,428 | 8/1978 | Farber | 542/437 |
| 4,119,776 | 10/1978 | Farber | 544/405 |
| 4,349,679 | 9/1982 | Garner et al. | 546/196 |
| 4,795,736 | 1/1989 | Hung et al. | 428/913 |
| 4,812,569 | 3/1989 | Eckstein | 548/456 |
| 4,897,494 | 1/1990 | Psaar | 548/455 |
| 4,931,567 | 6/1990 | Psaar | 548/455 |

OTHER PUBLICATIONS

Saxton, J. E., J. Chem. Soc. 3592 (1952).

Kiang, A. K. & Mann, F. G., J. Chem. Soc. 594 (1953).

Borsche, W. & Groth, H. Anralen, Chem. Abstr., vol. 37, 3754 (1943).

*Primary Examiner*—Cecilia Shen

*Attorney, Agent, or Firm*—Benjamin Mieliulis

[57] ABSTRACT

Preparation of novel symmetrical and unsymmetrical chromogenic di-[bis-(indolyl)ethylenyl]tetrahalophthalides is disclosed. Specifically these compounds are chromogenic di-[bis-(indolyl)ethylenyl]tetrahalophthalides of the formula

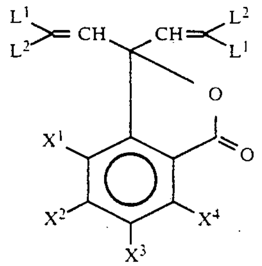

wherein L and X are as hereinafter defined.

The process disclosed involves condensing bis(indolyl)ethylenes with tetrahalophthalic anhydride in acetic anhydride, in the presence of an electron acceptor or preferably an acetate of Group I or II of the Periodic Table. Optionally, and preferably, where unsymmetrical di-[bis-(indolyl)ethylenyl]tetrahalophthalides are desired, indoles are reacted with an acylindole in the presence of a Vilsmeier reagent to form the starting bis(indolyl)ethylene.

12 Claims, No Drawings

PROCESS FOR PRODUCING DI[BIS-(INDOLYL)ETHYLENYL]TETRAHALOPHTHALIDES

This application is a continuation-in-part of U.S. Ser. No. 07/397,703, filed Aug. 23, 1989, now U.S. Pat. No. 4,970,308.

FIELD OF THE INVENTION

1. Background of Invention

This invention relates to chromogenic di-[bis(indolyl-)ethylenyl]tetrahalophthalides particularly methods for their preparation. These chromogenic compounds give intense colors when reacted with an electron accepting coreactant material. This invention relates to methods for the production of such chromogenic compounds useful in novel pressure-sensitive or heat-sensitive mark-forming record systems. As used in mark-forming systems, marking in desired areas on support webs or sheets may be accomplished by effecting localized reactive contact between the chromogenic material and the electron-accepting material on or in such web or sheet, such material being brought thereto by transfer or originally there in situ, the desired reactive contact forming colored images in the intended image marking areas.

2. Description of Related Art

Sheldon Farber, U.S. Pat. No. 4,119,776 issued Oct. 10, 1978, described vinyl phthalide color formers. Several divinyl phthalide chromogenic compounds (Cl) [(C) $L^1$, $L^2$=substituted phenyl] (read as Compound Cl arrived at by referring to formula C wherein $L^1$ and $L^2$ are as stated) have been prepared by the condensation of ethylenes (A1) [(A) $L^1$, $L^2$=substituted phenyl] with phthalic anhydrides (B) [(B) Each Halogen is independently Cl or Br] in acetic anhydride.

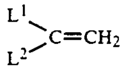
(A)

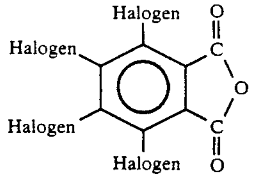
(B)

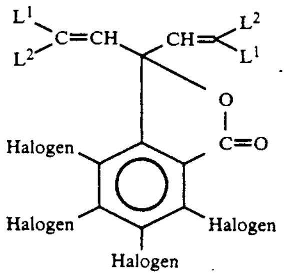
(C)

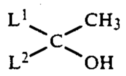
(D)

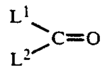
(E)

-continued

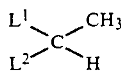
(F)

Substituted ethylenes (A1) or their precursors (D1) [(D) $L^1$, $L^2$=substituted phenyl] were prepared by the reaction of methylmagnesiumbromide (also known as methyl Grignard reagent) with ketons (E1) [(E) $L^1$, $L^2$=substituted phenyl]. The use of Grignard reaction to prepare (A1) imposes severe restrictions on the scale up synthesis of (A1) and consequently on the manufacture of divinyl phthalides (C1).

In another synthetic approach, the alcohol (D1) was obtained by reacting the ethane (F1) [(F) $L^1$, $L^2$=substituted phenyl] with lead peroxide in either nitric acid or formic acid; and the substituted ethylene (A1) was obtained from (D1) by dehydration [Yamada Kagaku, Japan Kokai 1988–8360, filed June 30, 1986].

When indole was heated with acetic anhydride containing 10% acetic acid a bis(indolyl)ethylene (A2) [(A) $L^1$,$L^2$=1-acetylindole-3-yl] was obtained as a by-product in 5–10% yield (J. E. Saxton, J. Chem. Soc., 3592 (1952)].

Substituted (2- and 1,2-) indoles when reacted with acetyl cyanide in the presence of hydrogen chloride yielded 1-cyano-1,1-di(indole-3-yl)ethanes (G) and these products can be converted to bis(indolyl)ethylenes (H) by heating them under vacuum either alone or with soda lime. In some cases, depending on the substituents M and W, (G) yields (H) on refluxing with aqueousethanolic 10% potassium hydroxide [A. K. Kiang and F. G. Mann, J. Chem., Soc., 594 (1953)].

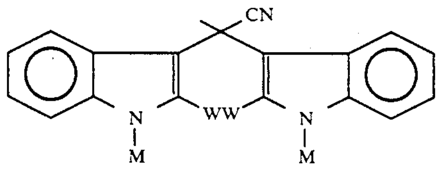
(G)

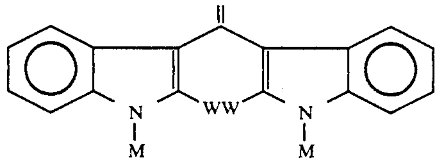
(H)

M = H, Ph
W = Me, Ph

Bis(indolyl)ethylene (Hl) [(H) M=H and W=Me] was speculated to be a product (m.p. 203° C.) from the reaction of 2-methylindole with ethyl acetate and sodium ethoxide. No other data were given to substantiate the structure [A. Angeli and G. Marchetti, Atti. Accad. Lincei, 16 (II), 179 (1907)].

In another report [W. Borsche and H. Groth, Annalen, 549, (1941)], 2-methylindole when boiled with acetyl chloride formed a product that on treatment with alkali gave a pseudobase, ($C_{20}H_{18}N_2$, pale rose, m.p. 208° C.). The pseudobase was suggested to be 1-(2-methylindole-3-yl)-l-(2-methyl-3-indolidene)ethane (H2) Again, insufficient data precludes the substantiation of this structure Furthermore, similar structure was proposed for the pseudobase obtained by substituting 2-phenylindole for 2-methylindole.

(H2)

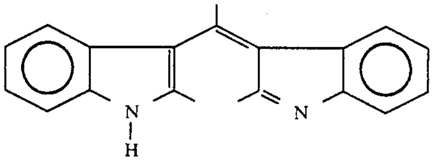

DESCRIPTION OF THE INVENTION

Preparation of novel symmetrical and unsymmetrical chromogenic di-[bis-(indolyl)ethyleneyl]tetrahalophthalides is disclosed. Specifically these compounds are chromogenic di-[bis(indolyl)ethylenyl]tetrahalophthalides of the formula (C)

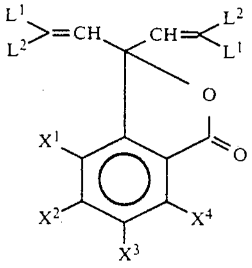

wherein each x is halogen, and preferably an independently selected from chlorine and bromine.

said method comprising condensing in at least 2:1 molar ratio bis-(indolyl)ethylene with tetrahalophthalic anhydride in acetic anhydride to form de-[bis(indolyl)ethyleneyl]tetrahalophthalide, said bis-indolyl ethylene being of the formula (A)

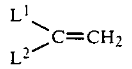

wherein each $L^1$ and $L^2$ herein is the same or different and is each independently selected from indole moieties (J1) through (J4), (J1)

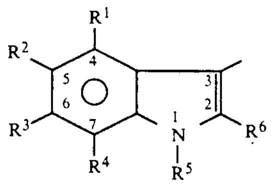

(J2)

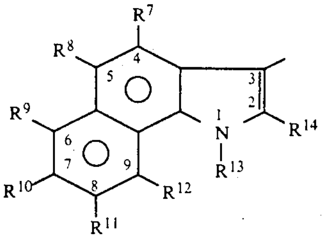

-continued (J3)

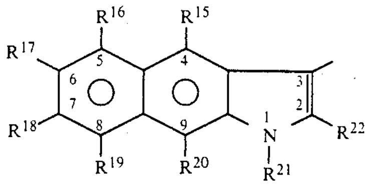

(J4)

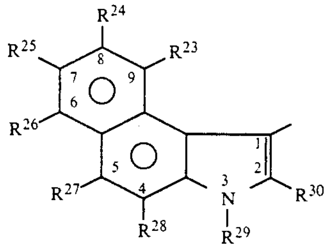

wherein in each of formulae (Jl) through (J4) each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl ($C_3$-$C_6$) (e.g. cyclohexyl, cyclopentyl, cyclobutyl and cyclopropyl), aroxyalkyl (e.g. β-phenoxyethyl), alkoxyalkyl (e.g. methoxyethyl), and aryl, wherein each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is independently selected from hydrogen, alkyl ($C_1$-$C_8$) cycloalkyl ($C_3$-$C_6$), aryl, halogen, alkoxy ($C_1$-$C_8$), aroxy, cycloalkoxy, dialkylamino including symmetrical and unsymmetrical alkyl groups with one to eight carbons, alkylcycloalkylamino, dicycloalkylamino,

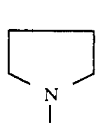 ; 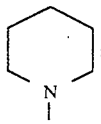 ; 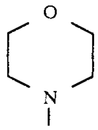 and 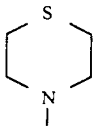 , wherein each alkyl moiety herein is from one to eight carbons, each cycloalkyl moiety is from three to six carbons.

It should be understood herein that all alkyl moieties, such as alkyl, or alkyl as part of aralkyl or alkoxyalkyl can be of at least one to eight carbons. Cycloalkyl groups preferably are of three to six carbons.

For clarity, the term "indoles" as used in this application is to be understood as referring to and including any of (J1), (J2), (J3) or (J4).

The term "bis(indolyl)ethylene" is understood as referring to and including formula (A).

The term "di-[bis-(indolyl)ethylenyl]tetrahalophthalide" refers to and includes formula (C).

Novel methods are disclosed for producing these di-[bis(indolyl)ethylenyl]tetrahalophthalides. The above formula, for ease of reference, can also be expressed as (C2) [(C) wherein each Halogen is independently selected from chlorine or bromine; wherein each L namely, $L^1$ and $L^2$ is the same or different and is each independently selected from indole moieties (J1)-(J4)]. This is read as new compound C2 arrived at by reference to formula C wherein $L^1$ and $L^2$ are as stated in the brackets.

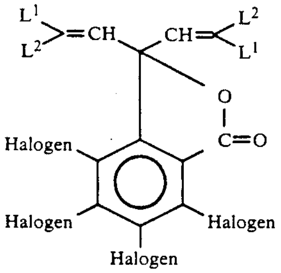
(C)

Preparation of di-[bis-(indolyl)ethylenyl]tetrahalophthalides (C2) comprises condensation of bis(indolyl-)ethylenes (A3) [(A) wherein each $L^1$ and $L^2$ is the same or different and is each independently selected from indole moieties (J1)-(J4)], with tetrahalophthalic anhydrides (B) in acetic anhydride with or without acetate of Group I or Group II elements of the periodic table.

A first synthetic route uses the corresponding indoles, acetic anhydride and Lewis acid such as zinc chloride or other electron acceptor preferably in approximately 1:1:0.5 molar ratios respectively in a suitable solvent. A second route uses the corresponding indoles with acetyl chloride preferably in approximately 1:(0.5–2.0) molar amounts at temperatures (15–75° C.) with or without solvent. A third route involves a condensation of any of components (K1)-(K4) with any of indoles (J1)-(J4) in the presence of a Vilsmeier reagent (such as phosphoryl chloride, phosgene, oxalyl chloride, benzoyl chloride, alkanesulfonyl chloride, arenesulfonyl chloride, alkyl chloroformate and aryl chloroformate) with or without solvent. This third route can be used to conveniently prepared unsymmetrical indolyl ethylenes (i.e. (A3) with differing $L^1$, $L^2$).

This third route is a method for the manufacture of chromogenic di-[bis-(indolyl)ethylenel]tetrahalophthalide of the formula

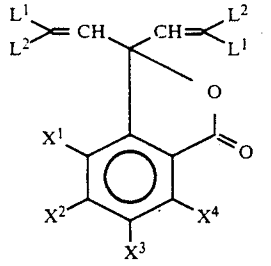

wherein each of $X^1$, $X^2$, $X^3$ and $X^4$ is independently selected from chlorine or bromine;

wherein each $L^1$ and $L^2$ herein is the same or different and is each independently selected from indole moieties (J1) through (J4),

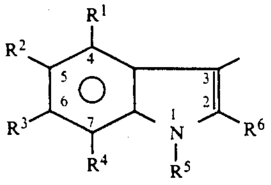
(J1)

-continued

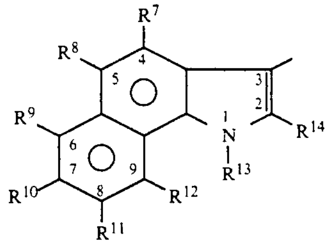
(J2)

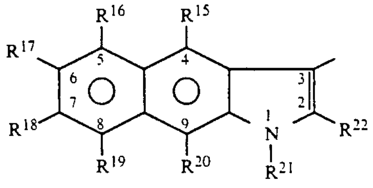
(J3)

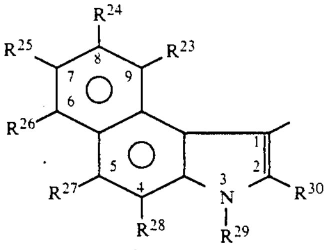
(J4)

wherein each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl ($C_3$-$C_6$), aroxyalkyl, alkoxyalkyl, and aryl, wherein each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is independently selected from hydrogen, alkyl ($C_1$-$C_8$), cycloalkyl ($C_3$-$C_6$), aryl, halogen, alkoxy ($C_1$-$C_8$), aroxy, cycloalkoxy, dialkylamino including symmetrical and unsymmetrical alkyl groups with one to eight carbons, alkylcycloalkylamino, dicycloalkylamino,

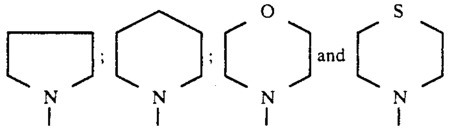

wherein each alkyl moiety herein is from one to eight carbons, each cycloalkyl moiety is from three to six carbons, said method comprising:

condensing acylindoles (K1) through (K4) with indoles (J1) through (J4) in the presence of a Vilsmeier reagent with or without solvent,

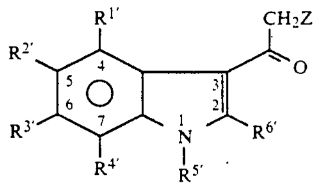
(K1)

-continued

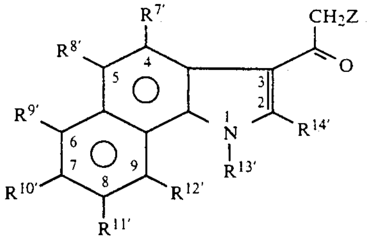

(K2)

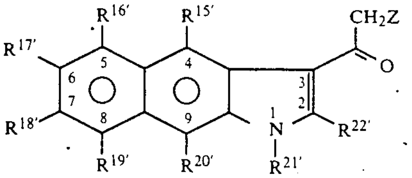

(K3)

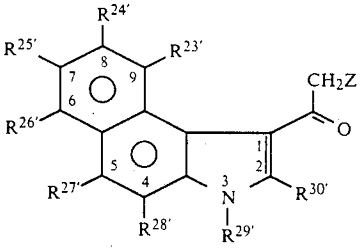

(K4)

wherein Z is hydrogen, R's are as previously defined with the proviso that the R's of (K1) through (K4) are independent of the R's of (J1) through (J4), so as to form bis(indolyl)ethylene then condensing such bis-(indolyl)ethylene with tetrahalophthalic anhydride in acetic anhydride to form di-[bis(indolyl)ethyleneyl]tetrahalophthalide.

It is to be understood the R's of (K1) through (K4) can be independent of the R's of (J1) through (J4). For example, $R^3$ in J1 can be selected as an alkyl while in K1, $R^3$ can be a different alkyl or halogen or even with moiety defined as possible for $R^3$.

$R^{1-30}=R^{1-30'}$ in terms of the moieties possible for each. The prime is added to (K1)-(K4) to further indicate the independence of the R's of (K1)-(K4) from the R's of (J1)-(J4).

Solvents as referred to herein are preferably organic and more preferably the halogenated organic solvents such as 1,2-dichloroethane and chlorobenzene and the like.

Di-[bis-(indolyl)ethylenyl]tetrahalophthalides (C2) are preparable from bis(indolyl)ethylenes (Al) and tetrahalophthalic anhydrides (B). In the first synthetic route bis(indolyl)ethylene (AI) and tetrahalophthalic anhydride (B) in 2:1 molar ratio respectively were heated at 100–110° C. in acetic anhydride for 2–3 hours. In the case of acid sensitive bis(indolyl)ethylene, acetate of Group I or Group II elements was added to the above reaction mixture to improve the yield of (C2). In another synthesis, the bis(indolyl)ethylene (A1) is generated in situ from the indole (J1)-(J4) and acetyl chloride with or without solvent and then condensed with tetrahalophthalic anhydride (B) in the presence of acetate of Group I or Group II elements and acetic anhydride at 100–110° C. for 2–3 hours. This procedure, referred to as one-pot two-step synthesis, has several advantages over the first route; for example, (a) it simplifies the process for the manufacture of di-[bis-(indolyl)ethylenyl]tetrahalophthalides (C2) by eliminating the isolation and purification of intermediate bis(indolyl)ethylenes; and (b) unstable or difficult to isolate bis(indolyl)ethylenes (A3) are condensed in situ with tetrahalophthalic anhydrides (B) to give (C2) that are difficult to prepare otherwise.

In the first described process of the invention, the bis(indolyl)ethylenes are prepared by condensing an indole, which can be substituted or unsubstituted with acid anhydride $[ZCH_2CO)_2O]$ in the presence of an electron acceptor or acidic type compounds. The electron acceptors are compounds such as carboxylic acids (e.g. acetic acid); or sulfonic acids (e.g. p-toluenesulfonic acid); or acid chlorides (e.g. benzoyl chloride); or Lewis Acids (e.g. zinc chloride, boron trifluoride). The reaction is accomplished in solvent, preferably organic, or more preferably the halogenated organic solvents such as 1,2-dichloroethane and chlorobenzene and the like.

All the described processes are conducive to scale-up and are used to prepare a variety of di-[bis(indolyl)ethylenyl] tetrahalophthalides (C2). Some examples are illustrated in Table 1.

This invention teaches a process for the preparation of chromogenic compounds which in color form have absorbance in the infrared region of the spectrum at approximately 700–1200 nm and thus are eligible for use in pressure-sensitive and thermal recording systems. Compounds which are chromogenic and absorptive in the near infrared region of the spectrum have commercial utility by being capable, when imaged, of being detected by optical reading machines. The colorable chromogenic compounds are eligible for use in pressure-sensitive recording and thermal recording systems. Advantageously recording systems utilizing these compounds can be read by optical reading machines, particularly those capable of reading for the infrared wavelength range of 700–1200 nm.

The colorable chromogenic compounds of the invention, can be combined with other chromogenic materials covering other or wider spectral ranges and can be used in pressure-sensitive and thermal recording systems to provide images which absorb over wider ranges of the electromagnetic spectrum. The commercial significance is that a larger assortment of available optical readers can thus be effectively useful with such imaged record systems.

Mixtures of the phthalides of this invention can be assembled. Mixtures of these chromogens which are grey, black or neutral can be useful in record systems, including carbonless and thermal systems. In thermal systems such mixtures have been suggested as reducing background. Such mixtures can be assembled using the compounds of this invention or in combination with other chromogens.

The chromogenic compounds of the invention also find use in photosensitive printing material, typewriter ribbons, inks and the like.

More specifically the process of the invention relates to the preparation of chromogenic compounds having two vinyl linkages. These compounds are substantially colorless or slightly colored solids but can be converted to colored forms upon reactive contact with an electron accepting material. The compounds of the invention in imaged or colored form are typically dark colored and are remarkably absorptive of near infrared light such that images formed of these compounds can be detected by conventional optical readers capable of detecting in the infrared wavelength range of 700–1200 nm.

In the invention di-[bis-(indolyl)ethylenyl]tetrahalophthalides (C2) [(C) wherein each halogen is independently selected from chlorine or bromine; wherein each L namely, $L^1$ and $L^2$ is the same or different and is each independently selected from indole moieties of the formulae (J1)-(J4)] are prepared. (C2) is understood or read to be compound (C) as described in the brackets and with reference to the formula set forth below.

The processes described for the preparation of (C2) are very conducive to scale up.

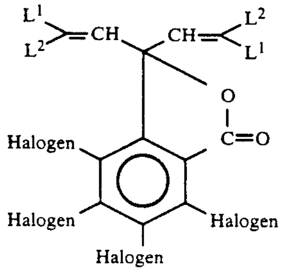

(C)

(J1) = $L^1$ or $L^2$ are as earlier defined herein. The halogen is each independently chlorine or bromine.

Each halogen is independently chlorine or bromine.

In forming pressure-sensitive or heat-sensitive mark forming record systems with di-[bis-(indolyl)ethylenyl]-tetrahalophthalides of the invention, the eligible acidic, or electron acceptor materials include, but are not limited to, acid clay substances such as attapulgite, bentonite and montmorillonite and treated clays such as silton clay as disclosed in U.S. Pat. Nos. 3,622,364 and 3,753,761, phenols and diphenols as disclosed in U.S. Pat. No. 3,539,375, aromatic carboxylic acids such as salicylic acid, metal salts of aromatic carboxylic acids as disclosed in U.S. Pat. No. 4,022,936 and acidic polymeric material such as phenolformaldehyde polymers as disclosed in U.S. Pat. No. 3,672,935 and oil-soluble metal salts of phenol-formaldehyde polymers as disclosed in U.S. Pat. No. 3,732,120. The compounds of this invention are useful as color formers in recording materials such as, for example, pressure-sensitive copying paper, thermally-responsive record material, electro heat-sensitive recording paper and thermal ink.

Pressure-sensitive copying paper systems provide a marking system and can be assembled by disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation, preferably comprises microcapsules containing liquid solvent solution. The microencapsulation process utilized can be chosen from the many known in the art. Well known methods are disclosed in U.S. Pat. Nos. 2,800,457; 3,041,289: 3,533,958; 3,755,190; 4,001,140 and 4,100,103. Any of these and other methods are suitable for encapsulating the liquid solvent containing the chromogenic compounds of this invention.

The chromogenic compounds of this invention are particularly useful in pressure-sensitive copying paper systems which incorporate a marking liquid comprising a vehicle in which is dissolved a complement of several colorless chromogenic compounds each exhibiting its own distinctive color on reaction with an eligible acidic record material sensitizing substance. Such marking liquids are disclosed in U.S. Pat. No. 3,525,630.

Thermally-responsive record material systems provide a marking system of color forming components which relies upon melting or subliming one or more of the components to achieve reactive, color-producing contact. The record material includes a substrate or support material which is generally in sheet form. Components of the color-forming system are in a substantially contiguous relationship, preferably substantially homogeneously distributed throughout a coated layer or layers of material deposited on the substrate. In manufacturing the record material, a coating composition is preferred which includes a fine dispersion of the components of the color-forming system, polymeric binder material, surface active agents and other additives in an aqueous coating medium.

The chromogenic compounds of this invention are useful in thermally-responsive record material systems either as single chromogenic compounds or in mixtures with other chromogenic compounds. Examples of such systems are given in U.S. Pat. Nos. 3,539,375 and 4,181,771.

Thermally-responsive record material systems are well known in the art and are described in many patents, for example U.S. Pat. Nos. 3,539,375; 3,674,535; 3,746,675; 4,151,748; 4,181,771; and 4,246,318 which are hereby incorporated by reference. In these systems, basic chromogenic material and acidic color developer material are contained in a coating on a substrate which, when heated to a suitable temperature, melts or softens to permit said materials to react, thereby producing a colored mark.

In the field of thermally-responsive record material, thermal sensitivity (response) is defined as the temperature at which a thermally responsive record material produces a colored image of satisfactory intensity (density). Background is defined as the amount of coloration of a thermally-responsive record material before imaging and/or in the unimaged areas of an imaged material. The ability to maintain the thermal sensitivity of a thermally-responsive record material while reducing the background coloration is a much sought after and very valuable feature.

One of the uses for thermally responsive record material which is enjoying increasing importance is facsimile reproduction. Alternative terms for facsimile are telecopying and remote copying. In the facsimile system, images transmitted electronically are reproduced as hard copy. One of the important requirements for thermally-responsive record material to be used in facsimile equipment is that it have good (low coloration) background properties.

Increases in the sensitivity of thermally-responsive record material have been achieved through the incorporation of a phenylhydroxynaphthoate compound or a hydroxyanilide compound in the color-forming composition along with the chromogenic material and developer material as disclosed in U.S. Pat. No. 4,470,057 or U.S. Pat. No. 4,535,347, respectively, by Kenneth D. Glanz. Such sensitizer materials can be advantageously used in combination with the present invention.

The record material includes a substrate or support material which is generally in sheet form. For purposes of this invention, sheets also mean webs, ribbons, tapes, belts, films, cards and the like. Sheets denote articles having two large surface dimensions and a comparatively small thickness dimension. The substrate or support material can be opaque, transparent or translucent and could, itself, be colored or not. The material can be fibrous including, for example, paper and filamentous synthetic materials. It can be a film including, for example, cellophane and synthetic polymeric sheets cast, extruded, or otherwise formed. The gist of this invention resides in the color-forming composition coated on the substrate. The kind or type of substrate material is not critical.

Although not required to practice and demonstrate the beneficial properties of the claimed invention, the inclusion of certain sensitizing materials in the color-forming system provides a further improvement in properties, especially increases in sensitivity. Materials such as 1,2-diphenoxyethane, N-acetoacetyl-o-toluidine, para-benzylbipbenyl; phenyl-1-hydroxy-2-naphthoate, stearamide and p-hydroxyoctadecanilide are useful as such sensitizing materials. A listing of additional sensitizers can be found in U.S. Pat. No. 4,531,140.

The components of the color-forming system are in a contiguous relationship, substantially homogeneously distributed throughout the color-forming system, preferably in the form of a coated layer deposited on the substrate. In manufacturing the record material, a coating composition is preferred which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as carnauba wax; synthetic waxes; lubricants such as zinc stearate; wetting agents and defoamers.

The color-forming system components are substantially insoluble in the dispersion vehicle (preferably water) and are ground to an individual average particle size of between about I micron to about 10 microns, preferably about 1 to about 3 microns. The polymeric binder material is substantially vehicle soluble, although latexes are also eligible in some instances. Preferred water-soluble binders include polyvinyl alcohol, hydroxyethylcellulose, methylcellulose, hydroxypropylmethylcellulose, starch, modified starches, gelatin and the like. Eligible latex materials include polyacrylates, polyvinylacetates, polystyrene, and the like. The polymeric binder is used to protect the coated materials from brushing and handling forces occasioned by storage and use of the thermal sheets. Binder should be present in an amount to afford such protection and in an amount less than will interfere with achieving reactive contact between colorforming reactive materials.

Coating weights can effectively be about 3 to about 9 grams per square meter (gsm) and preferably about 5 to about 6 gsm. The practical amount of color-forming materials is controlled by economic considerations, functional parameters and desired handling characteristics of the coated sheets.

DESCRIPTION OF THE PREFERRED EMBODIMENTS

In the following examples, general procedures for preparing certain di-[bis-(indolyl)ethylenyl]tetrahalophthalides of formula (C2) are described; and the examples are not intended to be exhaustive and the moieties, as previously-defined, are all eligible for use in any combination in preparing the compounds. Unless otherwise noted, all measurements, percentages and parts are by weight and in the metric system.

Satisfactory spectroscopic data were obtained for new compounds synthesized.

EXAMPLE 1

One-pot two-step preparation of 3.3-bis[1.1-bis(1-β-methoxyethyl-2-meyhlindole-3-yl)ethylene-2-yl]-4,5,6,7-tetrachlorophthalide Table 1, Entry 9

1-β-methoxyethyl-2-methylindole (19.0g,0.1 mole) was stirred with acetyl chloride (16.0g.0.2 mole) at room temperature for 5 hours. Sodium acetate (16.4g,0.2 mole), acetic anhydride (30 ml) and tetrachlorophthalic anhydride (7.2g,0.025 mole) were added to the reaction mixture and the reaction mixture was heated at 100° C. for two hours, cooled to room temperature, stirred with excess aqueous sodium hydroxide (10%) and toluene. After stirring for 30 minutes at 60° C., toluene layer was separated, washed twice with hot water, dried and concentrated. The residue was warmed with isopropanol and filtered. The product was purified by column chromatography on silica gel, followed by recrystallization from chloroform/isopropanol. Yield:- 11.3g(43%), pale yellow solid, m.p.:-140–142° C.

A solution of the product gives a greenish blue color to paper coated with a phenolic resin, with reflectance minima at 607 and 815 nm; and a blue color to paper coated with silton clay, with reflectance minima at 610 and 808 nm.

The calculated analysis for $C_{60}H_{58}N_4O_6Cl_4$, the title compound, is C,67.16%; H,5.45%; N,5.22%; and Cl,13.22%. Found on analysis: C,67.17%; H,5.44%; N,5.10%; and Cl,13.19%.

EXAMPLE 2

Preparation of 3.3-bis[l-(l-ethyl-2-methylindole-3-yl)-l-(l-β-methoxyethyl-2-methylindole-3-yl)ethylene-2-yl]-4.5.6.7-tetrachlorophthalide Table 1, Entry 20

1-(1-ethyl-2-methylindole-3-yl)-l-(l-α-methoxyethyl-2-methylindole-3-yl)ethylene (3.7g,0.01 mole) and tetrachlorophthalic anhydride(1.5g,0.005 mole) in acetic anhydride (15 ml) were heated at 120° C. for two hours, cooled down to room temperature and treated with aqueous sodium hydroxide(100 ml,10%) and toluene (100 ml). After vigorous stirring for 30 minutes, the toluene layer was separated, washed with hot water, dried and concentrated under reduced pressure. The residue was purified by chromatography on silica gel. The product obtained was heated with methanol, allowed to cool to room temperature and filtered; and, this process was repeated twice. Yield: 2.6g(51%), brown powder, m.p.:213–217° C.

A solution of the product gives a green color to paper coated with a phenolic resin, with reflectance minima at 612 and 808 nm; and bluish green color to paper coated with silton clay, with reflectance minima at 609 and 809 nm.

The calculated analysis for $C_{58}H_{54}N_4O_4Cl_4$, the title compound, is C,68.77%; H,5.37%; N,5.53%; and Cl,14.00%. Found on analysis: C,68.44%; H,5.15%; N,5.30%; and Cl,14.61%.

EXAMPLE 3

Preparation of 3.3-bis[l-(l-ethyl-2-methylindole-3-yl)-l-(l-β-methoxyethyl-2-methylindole-3-yl)ethylene-2-yl]-4.5.6.7-tetrachlorophthalide using 1,2-dichloroethane as solvent Table 1, Entry 2

1-(1-ethyl-2-methylindole-3-yl)-l-(l-β-methoxyethyl-2-methylindole-3-yl)ethylene (14.9g, 0.04 mole) and tetrachlorophthalic anhydride (5.7g, 0.02 mole) in acetic anhydride (20 ml) and 1,2-dichloroethane (20 ml) were heated at 85° C. for 4 hours, cooled down to room temperature and treated with aqueous sodium hydroxide (200 ml, 10%) and toluene (500 ml). After vigorous stirring for 30 minutes, the toluene layer was separated, washed with hot water, dried and concentrated under reduced pressure. The residue was chromatographed on silica gel using first toluene and then toluene:acetone::4:1 as eluents. Fractions containing the product were collected, combined and concentrated. The residue was heated in methanol and allowed to cool. The solid formed was filtered and recrystallized from toluene/methanol. Yield:-17.2g (85%), pale yellow solid, m.p.:- 218–220° C.

A solution of the product given a green color to paper coated with a phenolic resin, with reflectance minima at 613 and 812 nm; and bluish green color to paper coated with silton clay, with reflectance minima at 613 and 805 nm.

The calculated analysis for $C_{38}H_{54}N_4O_4Cl_4$, the title compound, is C, 68.77%; H,5.37%; N,5.53%; and Cl, 14.00%. Found on analysis: C,69.22%; H,5.40%; N,5.56%; and Cl, 14.10%.

TABLE 1

REFLECTANCE MINIMA AND COLOR OF 3,3-BIS(INDOLYLETHYLENYL)-4,5,6,7-TETRAHALOPHTHALIDES ON RESIN-COATED AND-SILTON-COATED PAPERS.

| ENTRY | COMPOUND | M.P. (°C.) | REFLECTANCE MINIMA (nm)* & COLOR ON RESIN-COATED | SILTON-COATED |
|---|---|---|---|---|
| 1 | 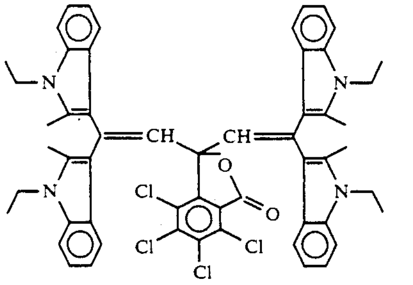 | 244–246 | 813 green | 806 blue |
| 2 | 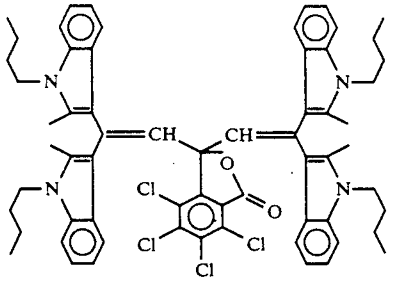 | 126–129 | 808 green | 806 blue |
| 3 | 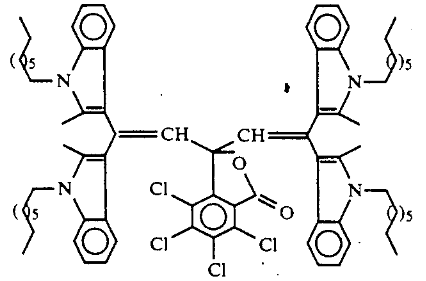 | 135–137 | 810 green | 804 blue |

TABLE 1-continued
REFLECTANCE MINIMA AND COLOR OF 3,3-BIS(INDOLYLETHYLENYL)-4,5,6,7-TETRAHALOPHTHALIDES ON RESIN-COATED AND SILTON-COATED PAPERS.
| ENTRY | COMPOUND | M.P. (°C.) | REFLECTANCE MINIMA (nm)* & COLOR ON RESIN-COATED | SILTON-COATED |
|---|---|---|---|---|
| 4 | 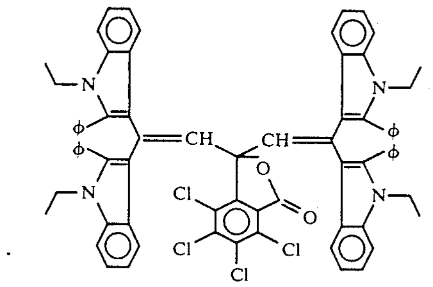 | 253-254 | 879 light green | 870 light green |
| 5 | 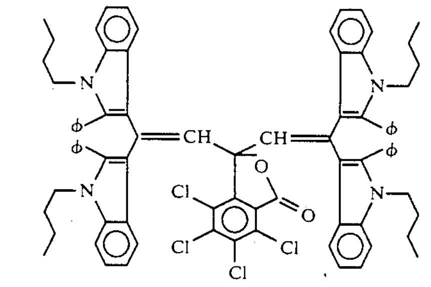 | 203-205 | 858 light green | 865 light green |
| 6 | 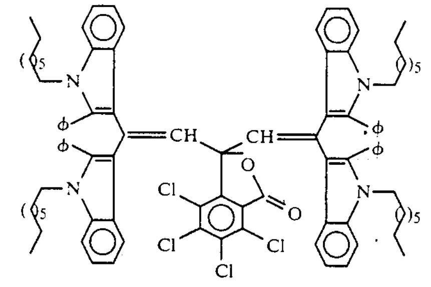 | 132-135 | 879 light green | 864 light green |
| 7 | 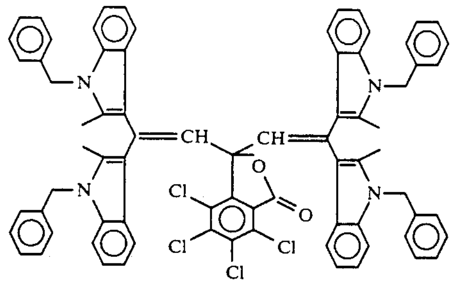 | 258-259 | 808 green | 809 green |
| 8 | 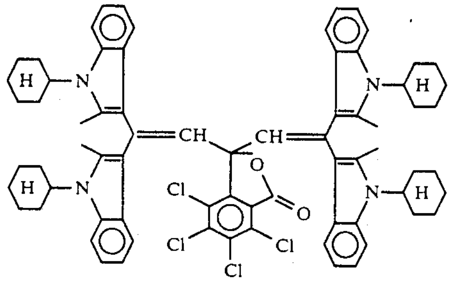 | 259-261 | 830 green | 830 green |

TABLE 1-continued
REFLECTANCE MINIMA AND COLOR OF 3,3-BIS(INDOLYLETHYLENYL)-4,5,6,7-TETRAHALOPHTHALIDES ON RESIN-COATED AND-SILTON-COATED PAPERS.
| ENTRY | COMPOUND | M.P. (°C.) | REFLECTANCE MINIMA RESIN-COATED | (nm)* & COLOR ON SILTON-COATED |
|---|---|---|---|---|
| 9 | 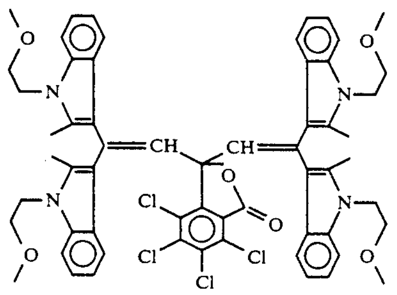 | 140–142 | 815 green | 808 bluish green |
| 10 | 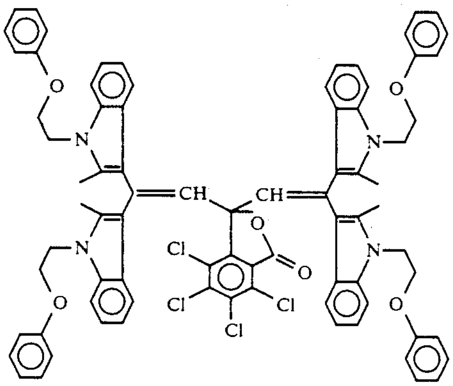 | 137–140 | 802 green | 822 green |
| 11 | 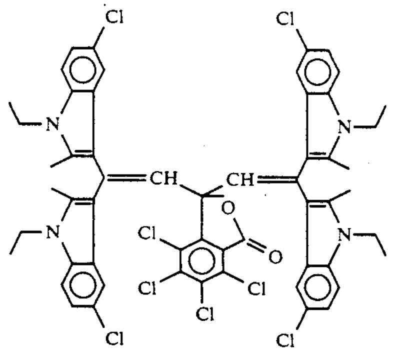 | 228–230 | 803 green | 799 blue |
| 12 | 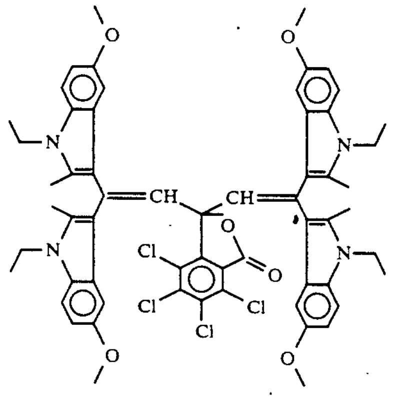 | 175–178 | 803 light blue | 794 blue |

TABLE 1-continued
REFLECTANCE MINIMA AND COLOR OF 3,3-BIS(INDOLYLETHYLENYL)-4,5,6,7-TETRAHALOPHTHALIDES ON RESIN-COATED AND-SILTON-COATED PAPERS.
| | | | REFLECTANCE MINIMA | (nm)* & COLOR ON |
|---|---|---|---|---|
| ENTRY | COMPOUND | M.P. (°C.) | RESIN-COATED | SILTON-COATED |
| 13 | 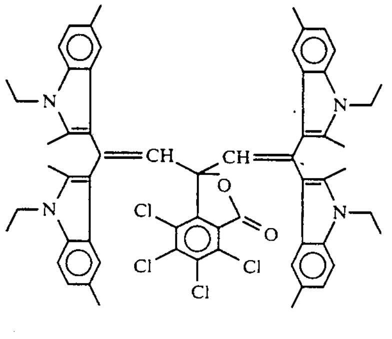 | 262-263 | 805 green | 812 blue |
| 14 | 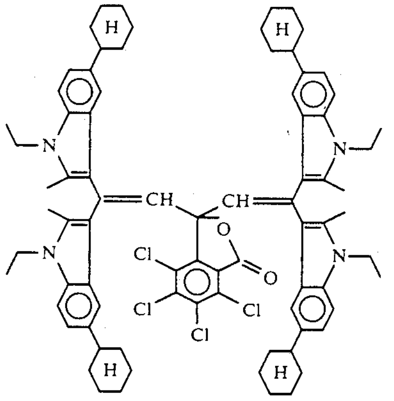 | 235-237 | 805 green | 808 bluish green |
| 15 | 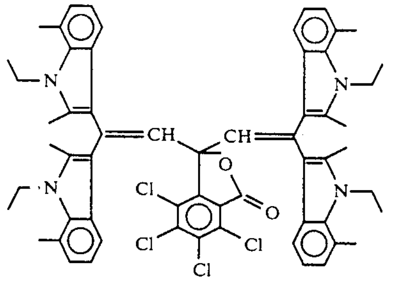 | 260-262 | 832 green | 827 bluish green |
| 16 | 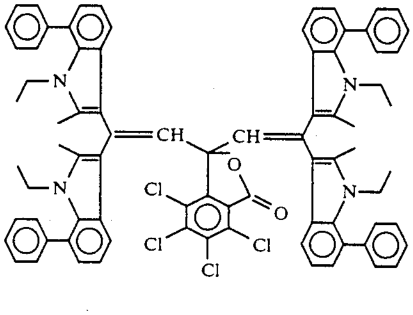 | 223-226 | 843 green | 832 bluish green |

TABLE 1-continued
REFLECTANCE MINIMA AND COLOR OF 3,3-BIS(INDOLYLETHYLENYL)-4,5,6,7-TETRAHALOPHTHALIDES ON RESIN-COATED AND-SILTON-COATED PAPERS.
| ENTRY | COMPOUND | M.P. (°C.) | REFLECTANCE MINIMA RESIN-COATED | (nm)* & COLOR ON SILTON-COATED |
|---|---|---|---|---|
| 17 | 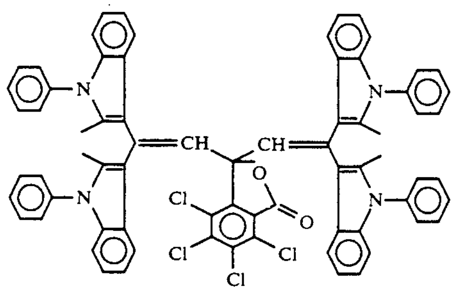 | 211–213 | 829 green | 818 green |
| 18 | 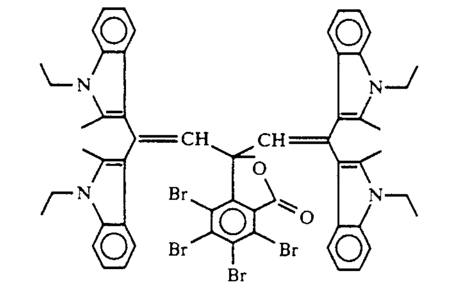 | 230–232 | 807 green | 805 blue |
| 19 | 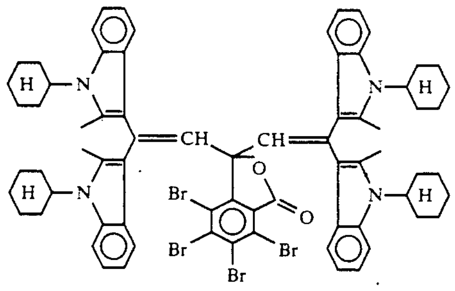 | 252–253 | 834 green | 829 green |
| 20 | 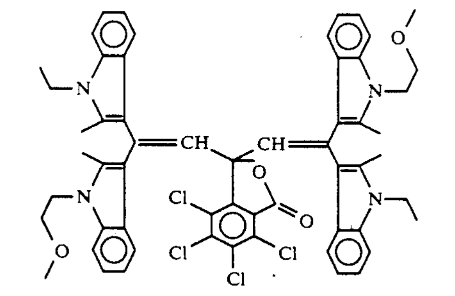 | 218–220 | 812 green | 805 bluish green |
| 21 | 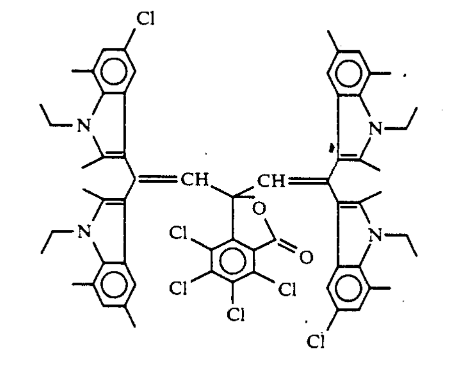 | 269–271 | 826 green | 826 green |

TABLE 1-continued

REFLECTANCE MINIMA AND COLOR OF 3,3-BIS(INDOLYLETHYLENYL)-4,5,6,7-TETRAHALOPHTHALIDES ON RESIN-COATED AND SILTON-COATED PAPERS.

| ENTRY | COMPOUND | M.P. (°C.) | REFLECTANCE MINIMA RESIN-COATED | (nm)* & COLOR ON SILTON-COATED |
|---|---|---|---|---|
| 22 | 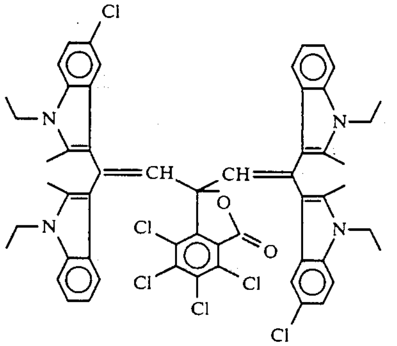 | 194–235 | 807 green | 803 blue |

*Near infrared region only

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

What is claimed is:

1. A process for the manufacture of di-[bis(indolyl)ethylenel]tetrahalophthalide comprising:
condensing indoles with acid anhydride and an electron acceptor selected from the group consisting of carboxylic acid, sulfonic acid, acid chloride and Lewis Acid in the presence of halogenated organic solvent, to form bis-(indolyl)ethylenes, in at least 2:1 molar ratio; and
condensing bis-(indolyl)ethylenes with tetrahalophthalic anhydride in acetic anhydride to form di-[bis(indolyl)-ethylenyl]tetrahalophthalide in at least 2:1 molar ratio.

2. The process according to claim 1 wherein the electron acceptor is selected from the group consisting of zinc chloride, boron trifluoride, benzoyl chloride, p-toluenesulfonic acid, and acetic acid.

3. The process according to claim 2 wherein the electron acceptor is zinc chloride.

4. The process according to claim 1 wherein the condensing of the bis-(indolyl)ethylenes with tetrahalophthalic anhydride in acetic anhydride is carried out in the presence of an acetate of Group I or Group II elements of the Periodic Table.

5. A process for the manufacture of di-[bis(indolyl)ethylenyl] tetrahalophthalide comprising reacting indoles with acetyl chloride, reaction being carried out at a temperature from 15–75° C. to form bis-(indolyl)ethylene; then condensing the bis-(indolyl)ethylene with tetrahalophthalic anhydride in acetic anhydride in the presence of an acetate of Group I or of the Periodic Table to form di[bis(indolyl)ethylenyl]tetrahalphthalide.

6. The process according to claim 5 wherein reacting the indoles with acetyl chloride is carried out in the presence of a solvent.

7. The process according to claim 5 wherein the solvent comprises acetic anhydride or acetic anhydride in combination with 1,2-dichloroethane.

8. A process for the manufacture of a chromogenic di-[bis(indolyl)ethylenyl]tetrahalophthalide of the formula

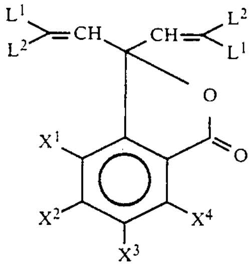

(C)

wherein each of $X^1$, $X^2$, $X^3$ and $X^4$ is independently selected from chlorine or bromine;
said process comprising condensing at least two bis-(indolyl)ethylenes with tetrahalophthalic anhydride in acetic anhydride to form di-[bis(indolyl)ethylenyl]tetrahalophthalide, said bis-indolyl ethylene being of the formula

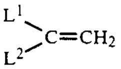

wherein each $L^1$ and $L^2$ herein is the same or different and is each independently selected from indole moieties (J1) through (J4),

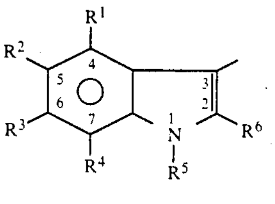

(J1)

-continued

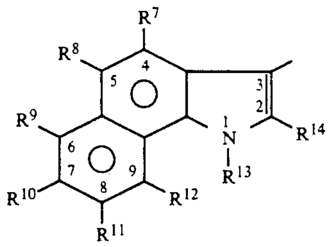
(J2)

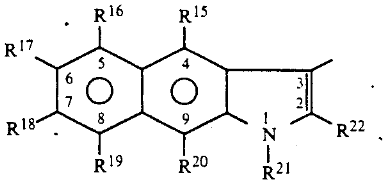
(J3)

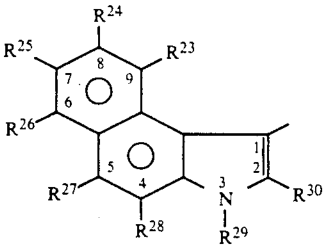
(J4)

wherein in each of formulae (J1) through (J4) each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl ($C_3$-$C_6$), cycloalkyl, aroxyalkyl, alkoxyalkyl, and aryl, wherein each of $R^1$, $R^2$, $R^3$, $R^4$, $R^7$, $R^8$, $R^9$, $R^{10}$, $R^{11}$, $R^{12}$, $R^{15}$, $R^{16}$,$R^{17}$,$R^{18}$, $R^{19}$, $R^{20}$, $R^{23}$,$R^{24}$, $R^{25}$,$R^{26}$, $R^{27}$ and $R^{28}$ need not be the same and is independently selected from hydrogen, alkyl ($C_1$-$C_8$), cycloalkyl ($C_3$-$C_6$), aryl, halogen, alkoxy ($C_1$-$C_8$), aroxy, cycloalkoxy, dialkylamino including symmetrical and unsymmetrical alkyl groups with one to eight carbons, alkylcycloalkylamino, dicycloalkylamino,

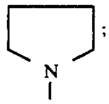 ; 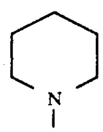 ; 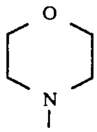 and 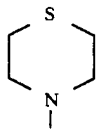 , wherein each alkyl moiety herein is from one to eight carbons, each cycloalkyl moiety is from three to six carbons.

9. The process according to claim 8 wherein the condensing of the bis-(indolyl)ethylene with tetrahalophthalic anhydride in acetic anhydride is carried out in the presence of an acetate of Group I or Group II elements of the Periodic Table.

10. A process for the manufacture of chromogenic di-[bis-(indolyl)ethylenyl]tetrahalophthalide of the formula

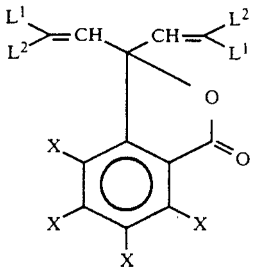

wherein each X is independently selected from chlorine or bromine;

wherein each $L^1$ and $L^2$ herein is the same or different and is each independently selected from indole moieties (J1) through (J4),

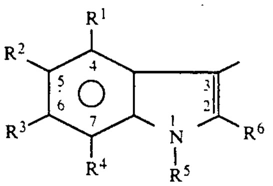
(J1)

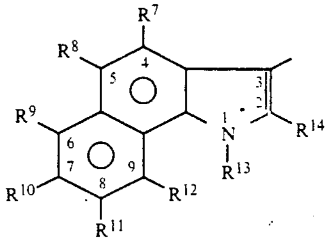
(J2)

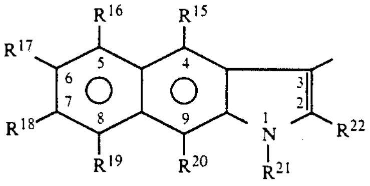
(J3)

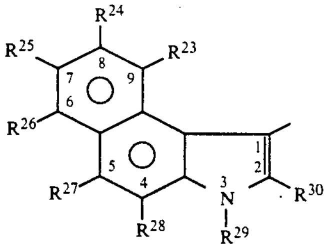
(J4)

wherein each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl ($C_3$-$C_6$), aroxyalkyl, alkoxyalkyl, and aryl, wherein each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is independently selected from hydrogen, alkyl ($C_1$-$C_8$), cycloalkyl ($C_3$-$C_6$), aryl, halogen, alkoxy ($C_1$-$C_8$), aroxy, cycloalkoxy, dialkylamino including symmetrical and unsymmetrical alkyl groups with one to eight carbons, alkylcycloalkylamino, dicycloalkylamino,

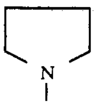
;
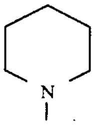
;
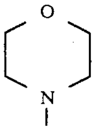
and
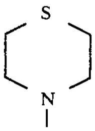
, wherein each alkyl moiety herein is from one to eight carbons, each cycloalkyl moiety is from three to six carbons, said method comprising:

condensing an acylindoles selected from (K1) through (K4) with an indole selected from (J1) through (J4) in the presence of a Vilsmeier reagent with or without solvent,

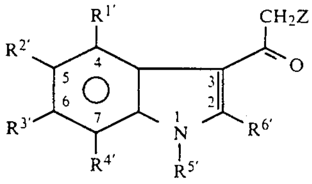
(K1)

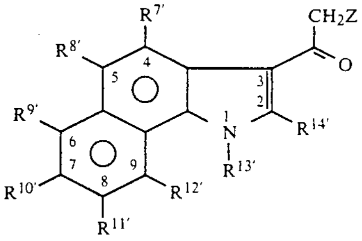
(K2)

-continued

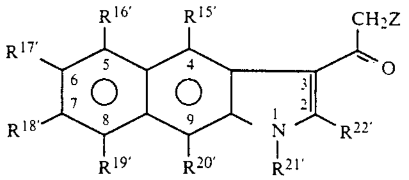
(K3)

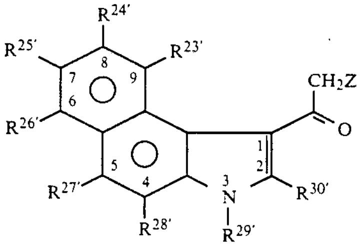
(K4)

wherein Z is hydrogen, R's are as previously defined with the proviso that the R's of (K1) through (K4) are independent of the R's of (J1) through (J4), so as to form bis(indolyl)ethylene then condensing such bis-(indolyl)ethylene with tetrahalophthalic anhydride in acetic anhydride to form di-[bis(indolyl)ethyl-enyl]tetrahalophthalide.

11. The process according to claim 10 wherein the Vilsmeier reagent is selected from the group consisting of phosphoryl chloride, phosgene, oxalyl chloride, benzoyl chloride, alkanesulfonyl chloride, arenesulfonyl chloride, alkyl chloroformate, and aryl chloroformate.

12. The process according to claim 10 wherein condensing the acylindoles is accomplished in the presence of 1,2-dichloroethane solvent.

* * * * *

UNITED STATES PATENT AND TRADEMARK OFFICE
CERTIFICATE OF CORRECTION

PATENT NO. : 5,039,821

DATED : August 13, 1991

INVENTOR(S) : Ponnampalam Mathiaparanam

It is certified that error appears in the above-identified patent and that said Letters Patent is hereby corrected as shown below:

Column 1, line 31 and 32. "Cl" appears at the end of both lines. The typeface selected for "l" in Cl is inconsistent throughout the printed patent. Note that "Cl" is intended and is correctly shown at the end of Column 2, line 13.

Column 2, line 33. Insert a space between "aqueous" and "ethanolic".

Column 2, line 60. Insert --238-- between "549," and "(1941)".

Column 3, line 36. Replace prefix "de" with "di".

Column 5, line 36. Delete "d" in "prepared".

Column 5, line 40. In the chemical name change "ethylenel" to --ethylenyl--.

Column 7, lines 34, 35. In the chemical name change "ethyleneyl" to --ethylenyl--.

Column 7, line 50. Replace "l" with --1-- in "Al" so it reads A1.

Column 7, line 52. Replace "I" with --1-- in "AI" so it reads A1.

Column 11, line 23. Replace "para-benzylbipbenyl;" with --para-benzylbiphenyl,--.

Column 12, line 17. Replace "meyhlindole" with --methylindole--.

Column 13, line 14. At the start of the line, replace "yll" with --yl]--.

Column 13, line 16. In the subtitle, change "Entry 2" to read --Entry 20--.

Column 14, line 13. Change "given" to --gives--.

Column 23, line 32, 33. In Claim 1 replace "di-[bis(indolyl)ethylenel]tetrahalophthalide" with --di-[bis(indolyl)ethylenyl]tetrahalophthalide--.

UNITED STATES PATENT AND TRADEMARK OFFICE
CERTIFICATE OF CORRECTION

PATENT NO. : 5,039,821

DATED : August 13, 1991

INVENTOR(S) : Ponnampalam Mathiaparanam

It is certified that error appears in the above-identified patent and that said Letters Patent is hereby corrected as shown below:

Column 23, line 62. In Claim 5, the next to last line, replace "di(bis(indolyl)ethylenyl)tetrahalphthalide" with --di(bis(indolyl)ethylenyl)tetrahalophthalide--.

Signed and Sealed this

Twenty-fourth Day of November, 1992

*Attest:*

DOUGLAS B. COMER

*Attesting Officer*

*Acting Commissioner of Patents and Trademarks*